United States Patent [19]

Shartle et al.

[11] Patent Number: 5,338,427

[45] Date of Patent: Aug. 16, 1994

[54] SINGLE USE SEPARATION CARTRIDGE FOR A CAPILLARY ELECTROPHORESIS INSTRUMENT

[75] Inventors: Robert J. Shartle, Livermore; Robert S. Dubrow, San Carlos, both of Calif.

[73] Assignee: Biometric Imaging Inc., Mountain View, Calif.

[21] Appl. No.: 23,088

[22] Filed: Feb. 26, 1993

[51] Int. Cl.$^5$ ............................................. C25B 9/00
[52] U.S. Cl. ............................................. 204/299 R
[58] Field of Search ................................. 204/299 R

[56] References Cited

U.S. PATENT DOCUMENTS

| | | | |
|---|---|---|---|
| 4,816,123 | 3/1989 | Ogan et al. | 204/183.3 |
| 4,902,132 | 2/1990 | Murphy, Jr. et al. | 356/339 |
| 4,906,344 | 3/1990 | Hjerten | 264/182.8 |
| 4,908,112 | 3/1990 | Pace | 204/299 R |
| 4,911,807 | 3/1990 | Burd | 204/180.1 |
| 4,985,129 | 1/1991 | Burd | 204/299 R |
| 5,006,309 | 4/1991 | Khalil et al. | 422/56 |
| 5,006,474 | 4/1991 | Horstman et al. | 436/524 |
| 5,009,503 | 4/1991 | Murphy, Jr. et al. | 356/339 |
| 5,037,523 | 8/1991 | Weinberger et al. | 204/299 R |
| 5,073,239 | 12/1991 | Hjerten | 204/180.1 |
| 5,120,414 | 6/1992 | Carson et al. | 204/299 R |
| 5,180,475 | 1/1993 | Young et al. | 204/299 R |
| 5,221,447 | 6/1993 | Hjerten | 204/299 R |

*Primary Examiner*—John Niebling
*Assistant Examiner*—Cybille Delacroix-Muirheid
*Attorney, Agent, or Firm*—Schneck & McHugh

[57] ABSTRACT

A disposable cartridge for a capillary electrophoresis instrument in which short capillary tube segments are used for simultaneous multiple lane separations. The cartridge contains all separation components of the instrument which come in contact with the sample and is capable of automatically loading a quantitative portion of a bulk sample into the capillary tube segments. Electrophoresis occurs without bulk flow through the capillaries, which are scanned in situ by the instrument.

43 Claims, 5 Drawing Sheets

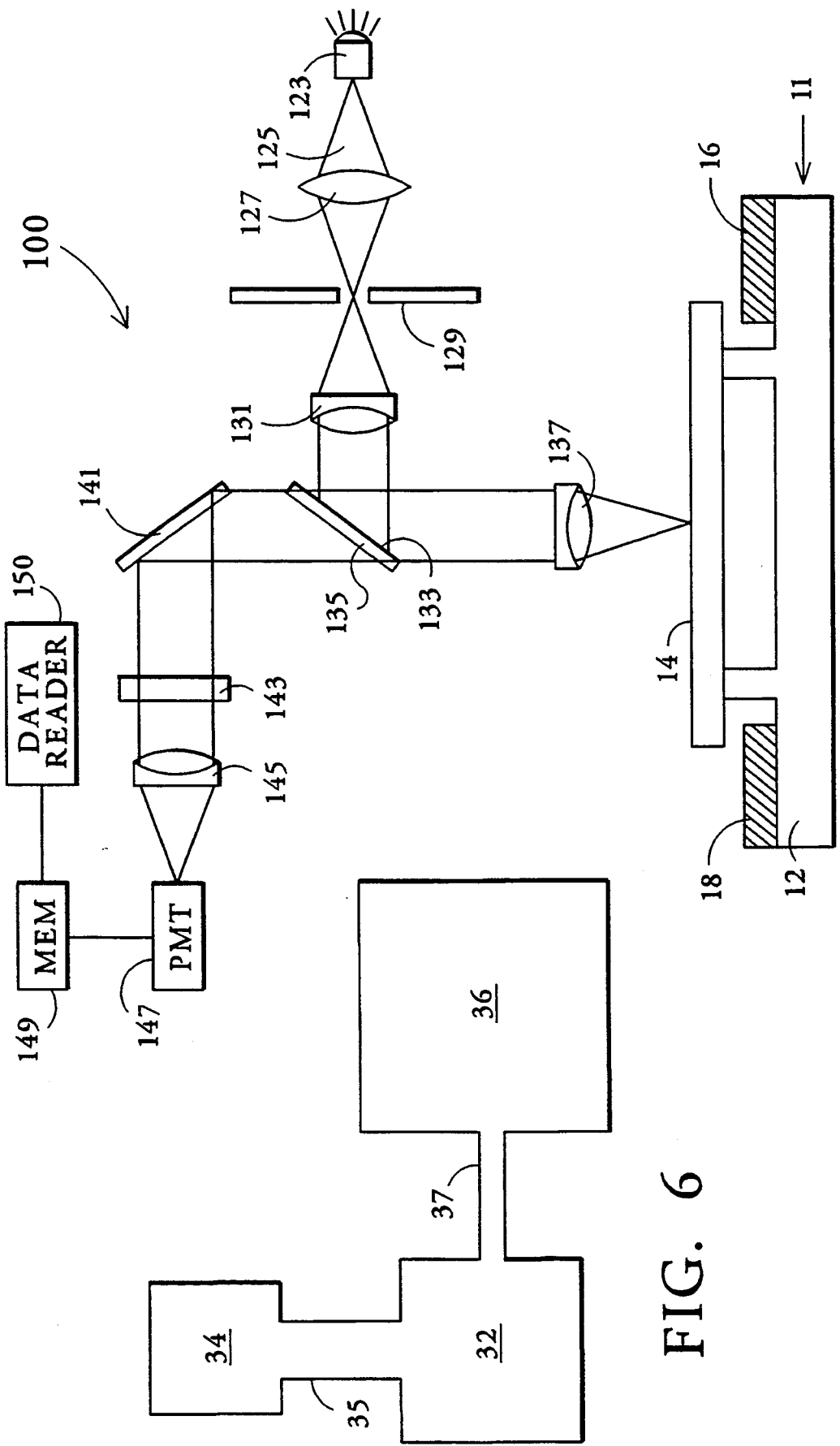

SINGLE USE SEPARATION CARTRIDGE FOR A CAPILLARY ELECTROPHORESIS INSTRUMENT

FIELD OF THE INVENTION

This invention relates to a disposable cartridge for use in an electrophoresis instrument, and in particular to a disposable multi-lane separation cartridge which contains all the separation components of an automated instrument which come in contact with the sample and includes the capability to quantitatively load a portion of the sample into the electrophoretic pathway.

BACKGROUND OF THE INVENTION

Electrophoretic separation techniques are based upon the differential mobilities of the components of a mobile phase passing through a stationary separation medium under the influence of an applied electric field. The components are distinguished by their migration times past a fixed point in the electrophoretic pathway or by their positions within the pathway at a fixed time. Capillary electrophoresis (CE) is one example of the former while capillary isoelectric focusing (IEF) is an example of the latter. The separation medium in free solution CE is the buffer filled capillary tube itself.

Instruments for performing capillary electrophoresis are frequently designed as flow-through systems. In IEF the separated components are commonly mobilized past a fixed detector following separation. The capillaries must also be washed between sample runs. In CE complicated hydraulic systems are required to accurately control sample introduction. A component's velocity is the vector sum of the bulk flow velocity, due to electroosmotic force, and the component's electrophoretic velocity. In capillary IEF, tubes are typically coated on their interior surface to eliminate electroosmosis and buffer reservoirs of high pH at the anode and low pH at the cathode are located at either end of the capillary tube. Components are focused within a stationary pH gradient to their isoelectric points and then mobilized by a variety of methods past a detector. CE capillaries vary in length from 70 mm to 1000 mm, with longer lengths used to improve resolution at the price of increased run time. IEF capillaries are typically 20–100 mm in length. Flow-through systems typically employ one capillary and can only separate one sample at a time. Additional controls, calibrators, and samples must be run sequentially. The use of long capillaries in CE, and the requirement for mobilization past a detector in IEF, greatly increase analysis time per sample.

Automated systems designed to perform multiple runs on different samples require wash cycles between runs. This significantly increases the volume of liquid waste produced. Reservoirs are required for wash solutions, waste and reagent which must be monitored and serviced by trained personnel. If the sample contains biohazardous material then waste disposal and instrument contamination become additional problems. Cross contamination resulting from electrode contamination is a particular problem. Auto-samplers which quantitatively load a sample into the system are typically designed to operate sequentially on samples and generally incorporate a wash cycle between samples.

Cartridges containing a capillary tube for insertion into a capillary electrophoresis instrument are known. U.S. Pat. No. 4,985,129 to Burd discloses a planar cartridge containing a looped capillary and a pair of aligned windows between which a segment of the capillary tube passes for zone detection. The cartridge is designed to connect the capillary tube ends to external reservoirs. U.S. Pat. No. 5,037,523 to Weinberger et al. discloses a similar cartridge further including air cooling slots in the cartridge body and annular electrodes surrounding the capillary tube ends. The cartridge is also designed to connect the capillary tube ends to external reservoirs.

U.S. Pat. No. 4,816,123 to Ogan et al. discloses a method for forming capillary electrophoresis channels using a wire or capillary tube as a template strand. Detectors are positioned next to the template strand prior to molding a plastic material around the template strand and detectors.

U.S. Pat. No. 4,908,112 to Pace discloses a capillary sized conduit constructed by covering an etched channel in a silicon wafer with a glass plate. Reservoirs are located at either end of the channel which is intersected by a second channel used for sample introduction. Electrodes are located throughout the system so that liquids may be moved by electroosmosis. Multiple channels, which are filled with a gel preparation fluid by capillary action from overhead reservoirs containing electrodes, are also disclosed. The reservoirs are then filled with buffer and a sample is injected into the reservoir with a volumetric syringe. The electroosmotic channels are less than 100 $\mu$m in cross-sectional dimension while the gel-filled channels are greater than 100 $\mu$m in cross-sectional dimension. None of the prior art devices contain only those portions of the electrophoretic separation system which contact the sample.

Devices for sample loading in capillary electrophoresis are known. U.S. Pat. No. 4,911,807 to Burd discloses a cassette having short capillary segments which are sequentially introduced into an electrophoretic pathway for sample loading or fraction collecting. U.S. Pat. Nos. 4,906,344 and 5,073,239 to Hjerten disclose thermal and electroendosmotic pumping means respectively for quantitative sample injection in capillaries. Mechanical pumps are also frequently employed. All of these devices require external manipulation of the system by some means to produce a quantitative sample load.

Use of one or more absorbent materials to provide motive force to fluid samples in disposable assay devices is disclosed in U.S. Pat. Nos. 5,006,309 to Khalil et al. and 5,006,474 to Horstman et al. Khalil et al. disclose an immunoassay device in which an absorbent material pulls fluid through an immobilizing fiber matrix where the results of the assay can be read. Horstman et al. disclose a device where two absorbent materials cause lateral bi-directional flow through a chromatographic separation material. Neither device uses a differential rate of flow to quantitatively load a sample into a fixed volume.

Most capillary electrophoresis instruments are flow-through devices which generate large volumes of waste relative to the effective separation volume of the capillaries. A significant portion of this waste volume arises from the need to wash those portions of the system which come in contact with the sample. These include the sample loaders, electrodes, buffer reservoirs and capillaries. These devices are generally incapable of running simultaneous multiple lane separations.

An object of the invention is to provide a single use separation cartridge containing all of those portions of an electrophoretic separation system which contact the sample.

Another object of the invention is to provide a single use separation cartridge which is capable of automatic quantitative sample loading.

A further object of the invention is to provide a single use separation cartridge that uses capillary forces to quantitatively introduce sample and buffers into the capillary.

A further object of the invention is to provide a single use separation cartridge that replaces large sample reservoirs with hemispherical drops of sample and buffer.

A further object of the invention is to provide a single use separation cartridge that contains all necessary reagents, wash solutions and waste receptacles.

SUMMARY OF THE INVENTION

The above objects have been achieved in a cartridge containing short capillary tube segments suspended by a planar support structure. The capillary tube ends are located adjacent to electrodes formed on the support. When liquid is placed in a gap between the electrode and one of the capillary tube ends the capillary tube segment is filled with liquid by capillary action. A selectively absorbent material located on the support structure which is in fluid communication with the gap slowly removes any excess liquid from the gap. A viscous, electrically conductive substance which minimizes hydrodynamic flow is then placed in each gap electrically bridging the capillary tube to the electrodes. The viscous substance, which is not absorbed by the selectively absorbent material, inhibits hydrodynamic flow in the capillary tube segment.

In one embodiment the capillary tube segments are horizontally positioned in a coplanar array on raised portions of the support. The capillary tube ends are located above thin film electrodes formed on the support. Capillary action fills the capillary tube segment when a drop of liquid is placed on the electrode surface. The electrode material and solution properties are chosen to produce a non-wetting condition such that the drop edge has a non-zero contact angle and the drop is confined to the application point. A small hole in the electrode fluidly communicates with an absorbent material located between the electrodes and the underlying support. After application of a drop of a viscous electrically conductive substance at each tube end, the cartridge is positioned in an electrophoresis instrument where the electrodes are connected to an external voltage supply in such a way to avoid contamination of the electrode contacts. In the preferred embodiments, fluorescently labeled substances in transparent capillary tube segments are optically detected by the instrument in situ following electrophoresis.

An advantage of the single use separation cartridge of the present invention is that it contains all of those separation portions of an electrophoretic system which contact the sample.

Another advantage is that the separation cartridge is capable of automatic quantitative sample loading.

A further advantage is that the single use separation cartridge contains all necessary reagents, wash solutions and waste receptacles.

A further advantage is that the single use separation cartridge uses capillary forces to quantitatively introduce sample and buffers into the capillary.

A further advantage is that the single use separation cartridge replaces large sample reservoirs with hemispherical drops of sample and buffer.

BRIEF DESCRIPTION OF THE DRAWINGS

FIG. 2b is a longitudinal cross-sectional view along line 2b of FIG. 2a;

FIG. 2c is a transverse cross-sectional view along line 2c of FIG. 2a;

FIG. 6 is a schematic representation of the auto-loading system;

FIG. 7 is a plan view of an electrophoresis instrument optically scanning the cartridge of FIG. 1;

DETAILED DESCRIPTION OF THE INVENTION

Figure 1:
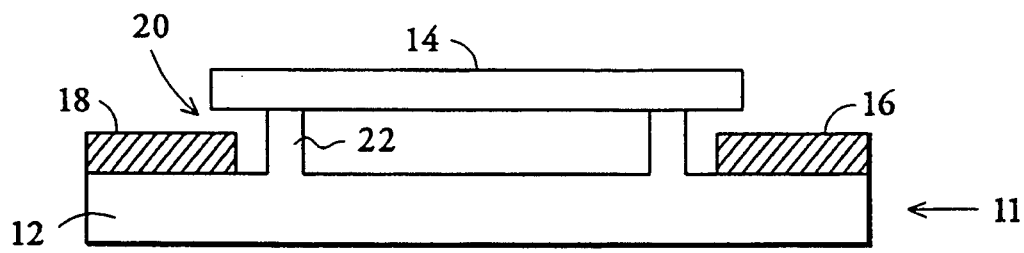
FIG. 1 is a side plan view of a horizontal embodiment of the present invention in which the capillary tube ends are located above the electrodes.

With reference to FIG. 1, a plan view of a horizontal embodiment in which the capillary tube ends are located above electrodes 16 and 18 is shown. Support structure 12 has a pair of pedestals 22 which position capillary tube 14 above planar electrodes 16 and 18 with the majority of its exterior surface surrounded by air.

In preferred embodiments, support structure 12 is a generally planar rectangular block of electrically insulating material. In one preferred embodiment support structure 12 has raised edges or pedestals on its upper surface from which capillary tube 14 is suspended. In other embodiments of the invention support structure 12 is a laminated structure composed of coplanar film sheets.

Capillary tube 14 may be made of any clear, low reflection, low absorbance material such as plastic, glass or silica and may be coated on the interior surface to prevent electroosmosis. Borosilicate glass is used in one preferred embodiment. Capillary tube 14 is usually from about one to about ten cm in length, although longer length may be used. Three to six cm lengths and 0.025 to 0.1 mm i.d.s are preferred. In preferred embodiments, capillary tube 14 has a round or rectangular cross-sectional configuration. If capillary tube 14 is rectangular and is to be optically scanned, a large aspect ratio is preferred. Any cross-sectional configurations having a large enough surface area to volume ratio to dissipate the heat generated during electrophoresis may also be used. The cross-sectional configuration of capillary tube 14 may be symmetrical or asymmetrical in shape and/or material. In some embodiments, the capillary is formed by ultrasonically welding two injection molded plastic parts together.

Electrodes 16 and 18 may be electrically conductive wires, if positioned coaxially to capillary tube 14, or planar when located beneath the tube ends. Electrodes 16 and 18 are metalized, or homogenously conductive, plastic films in preferred embodiments, although any planar conductive material may be used. The electrodes may also be plated directly on support structure 12.

In operation capillary tube 14 is filled with a conductive solution by capillary action. The conductive solution is usually a buffer which may contain additives, such as a surfactant, to inhibit electroosmosis. In the preferred embodiment capillary tube 14 is filled by capillary action after being attached to support structure 12 by placing a drop of solution onto the surface of electrode 16 or 18. The contact angle between the drop and the electrode material must be $>0°$ to confine the drop edge and not wet the electrode surface. Alternatively, capillary tube 14 may be filled before being placed on support structure 12 by placing one end into a solution.

When capillary tube 14 is used for capillary electrophoresis (CE) it is first filled with a buffer solution by placing a drop of buffer at one end. In preferred embodiments a drop of sample solution is then placed at the other end and sample is loaded using electrokinetic injection. When capillary tube 14 is used for isoelectric focusing (IEF) it is filled with a mixture containing the sample and carrier ampholytes in buffer. In both cases, following removal of excess solution, a drop of a viscous conductive substance which inhibits hydrodynamic flow is then placed onto the surface of electrodes 16 and 18 at each end of capillary tube 14. The viscosity of the drops in preferred embodiments is 220 centipoise although viscosities $\leq 1$ cp will decrease the hydrodynamic flow rate. In a 3 cm capillary tube having a 100 micron interior diameter the hydrodynamic flow due to surface tension and gravitational forces in 220 cp drops is reduced to 0.03 cm/min. Addition of a surfactant will lower the surface tension and thereby lower the internal pressure of the drops which is a driving force for hydrodynamic flow.

Electrodes 16 and 18 are connected to an external voltage supply when cartridge 11 is placed in the electrophoresis instrument. In IEF, after separation is complete, capillary tube 14 is scanned by the instrument. In CE separated components migrate past a fixed detector. Optical detection of fluorescently labeled components is used in a preferred embodiment. Any other well known detection method, such as UV absorbance, may also be used.

Figure 2A:
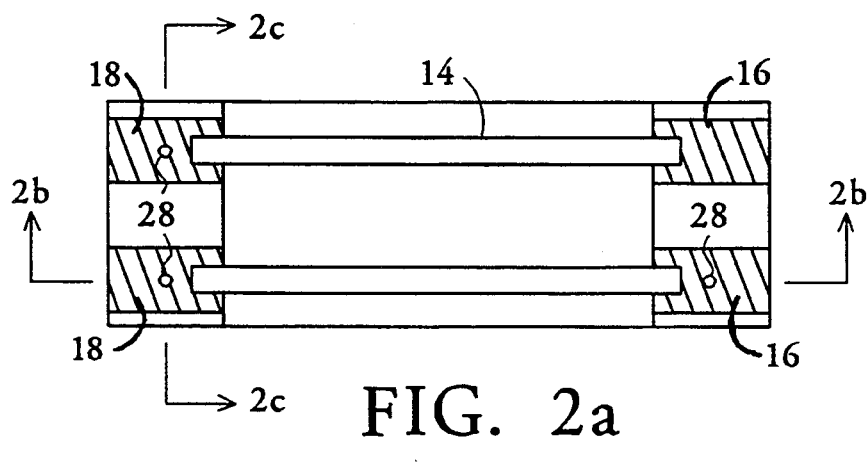
FIG. 2a is a top view of a multi-lane laminated cartridge of the present invention.
Figure 2B:
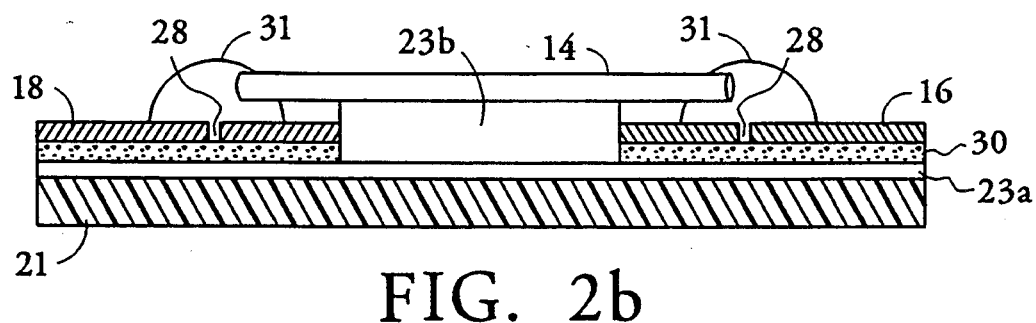
Figure 2C:
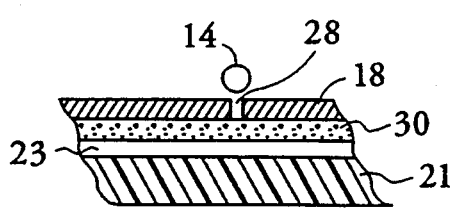

With reference to FIGS. 2a-c, the plan view of a second horizontal embodiment in which cartridge 11 is constructed by laminating planar films is shown. In this preferred embodiment, support structure 12 is a laminated, generally rectangular, block incorporating five coplanar sheets of a variety of films. A base sheet of acrylic film 21, 0.030" in thickness, is covered with a 0.003" thick adhesive sheet of double stick polyethene 23a. A second adhesive sheet of double stick polyethene 23b, 0.012" thick having a length equal to or less than the length of capillary tube 14 is centrally placed. An absorbent sheet of cellulose filter paper 30, 0.005" in thickness, is placed on adhesive sheet 23a at either end of adhesive sheet 23b. A conductive polymer sheet, 0.004" in thickness, is placed atop absorbent sheet 30 at either end of capillary 14 forming electrodes 16 and 18. A hole 28 in the conductive polymer sheet may be located at one or both ends of capillary 14. A drop of solution 31 is shown at either end of capillary tube 14. The solution may be buffer, sample, or a viscous electrically conductive substance. The diameter of hole 28 is much smaller than the base diameter of drop 31. Capillary tube 14 is adhesively attached to the laminate by adhesive sheet 23b.

Figure 3:
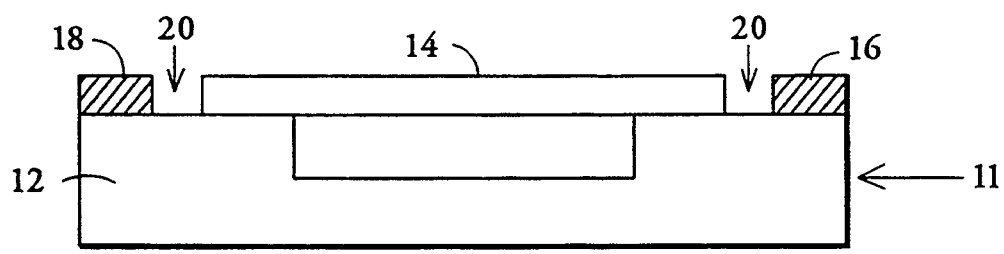
FIG. 3 is a side plan view of a horizontal embodiment of the present invention with axially aligned electrodes.

With reference to FIG. 3, a plan view of a horizontal embodiment of the present invention is shown. Cartridge 11 consists of a support structure 12 which horizontally positions a capillary tube 14 between a pair of electrodes 16 and 18. Electrodes 16 and 18 are each separated from the adjacent capillary tube end by a gap 20. Support structure 12 is an acrylic block and the ends of capillary tube 14 and wire electrodes 16 and 18 are located in V-shaped channels in the upper surface of the opposed raised edges of the block.

Figure 4:
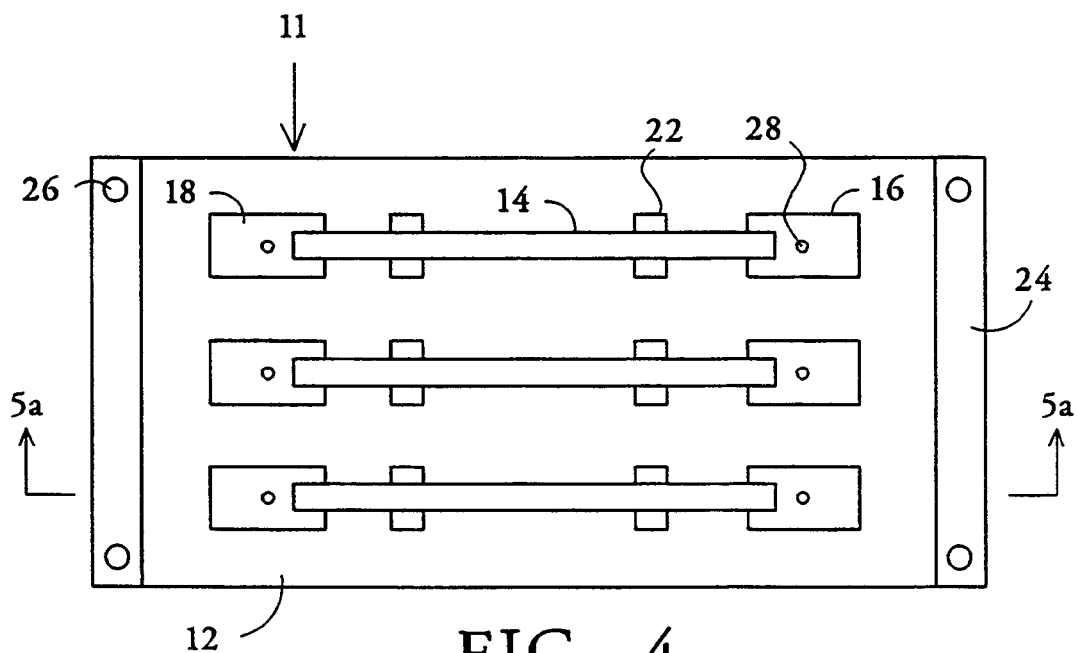
FIG. 4 is a top view of a multi-lane cartridge of the present invention.

With reference to FIG. 4, a top view of a multi-lane cartridge 11 is shown. Three capillary tubes 14 are horizontally disposed in a coplanar array by support pedestals 22 of support structure 12. Comparison of lane to lane results is facilitated when capillary tubes 14 have identical lengths and cross-sectional dimensions. Thin-film electrodes 18 and 16 are located beneath opposite ends of each capillary tube 14. Support structure 12 has a pair of opposed elevated edges 24. Each edge contains a pair of spaced apart apertures 26 which may be used as detents to index the location of cartridge 10 in the electrophoretic instrument. Each thin-film electrode 16 and 18 has a hole 28 passing through it to provide fluid communication between the surface of thin-film electrodes 16 and 18 and an absorbent material located beneath the electrodes, not shown.

Figure 5A:
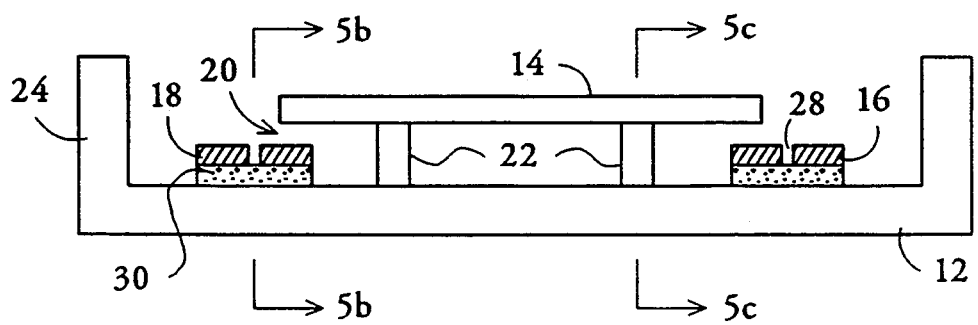
FIG. 5a is a longitudinal cross-sectional view of one lane of the cartridge along line 5a of FIG. 4.
Figure 5B:
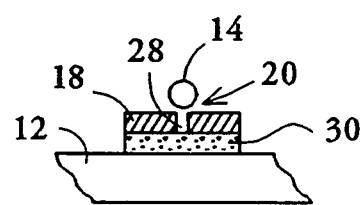
FIG. 5b is a transverse cross-sectional view along line 5b of FIG. 5a showing one end of the capillary tube.
Figure 5C:
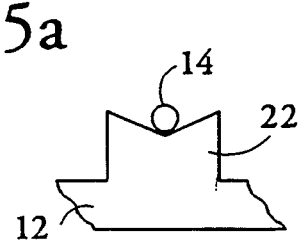
FIG. 5c is a transverse cross-sectional view along line 5c of FIG. 5a showing a grooved capillary support.

Referring now to FIG. 5a a cross-sectional view along line 5a of FIG. 4 is shown. An absorbent material 30 is located beneath electrodes 16 and 18 and in fluid communication through hole 28 with the surface of electrodes 16 and 18 and gaps 20. When performing IEF only the electrode located at the sample injection end needs to be in fluid communication with absorbent material 30. FIG. 5b is a transverse cross-sectional view along line 5b of FIG. 5a showing the relationship between the components located at one end of capillary tube 14. FIG. 5c is a transverse cross-sectional view along line 5c of FIG. 5a showing capillary tube 14 lying in a V-shaped groove in support pedestal 22. The position of capillary tubes 14 in relation to apertures 26 allows the electrophoretic instrument to optically scan the length of capillary tube 14. Precise positioning of the axis of capillary tube 14 is not critical as the optical system has the ability to track in the x, y and z axis.

Referring now to FIG. 6, a schematic representation of the auto-loading system is shown. When a bulk sample is placed in first reservoir 32 a quantitative portion is rapidly loaded into pathway 34 by auto-loading means 35. The remainder of the sample is slowly transported to a second reservoir 36 by draining means 37 where it is held leaving first reservoir 32 empty and a quantitative portion of the sample loaded into pathway 34. Autoloading means 35 is filling of a fixed volume by capillary action or electrokinetic pulse injection in the preferred embodiments. Other well known means by which a discrete quantitative portion of the sample is rapidly moved from first reservoir 32 into pathway 34, such as hydrodynamic or thermal injection, may also be used.

With reference to FIG. 7, an electrophoresis instrument 100 optically scanning a horizontally disposed cartridge 11 is shown. A strongly emitting light source, such as light emitting diode or laser 123 is used to generate a beam 125. LED 123 has an output power of about 50 milliwatts and a wavelength band which will excite fluorescence in the fluorescent labeling material. Such excitation radiation is known as actinic radiation. The beam is intercepted by a focusing lens 127 which directs the beam through a slit aperture and barrier 129. Light emerging from the slit is divergent and is intercepted by a collimating lens 131. The beam is then directed onto a reflecting surface 133 which is part of a dichroic mirror 135.

Dichroic mirror 135 is chosen to selectively reflect light at the wavelengths emitted by light source 123 while transmitting light at the wavelengths emitted by the fluorescent label. The reflected beam is directed toward a focusing lens 137. Light passing through the focusing lens carries an image of the slit 129 which is directed onto capillary 14. The image of slit 29 can be scanned along the longitudinal axis of capillary 14 by moving separation cartridge 11 relative to lens 137.

Fluorescent light emitted by a label, and some reflected light from the capillary, travel in a retrobeam to focusing lens 137. Note that the focusing lens is used by light traveling in each direction. From there, the retrobeam is directed to reflecting surface 133 which is a part of dichroic mirror 135. Light reflected from the capillary is reflected toward light source 123 while fluorescent light is passed through. The fluorescent light is then directed by a mirror 141 through a filter 143 which rejects any light other than the desired wavelength from the fluorescent label. Light transmitted through the filter is directed toward a focusing lens 145. From there the beam is directed to a light detector, such as photomultiplier tube 147 with a slit located at the image plane of the separation medium. The focused locations of the label are measured relative to one end of the capillary.

The output of photomultiplier tube 147 is maintained in a buffer memory 149. A data reader 150 is connected to the buffer memory 149 for receiving recorded signals which represent the fluorescent peaks. The data reader is a computer which correlates the various peaks.

In multi-lane embodiments, one end of each of capillary tubes 14 may be located above a common thin-film electrode 16. In this embodiment each capillary tube 14 may be subjected to a separate voltage difference between each of electrodes 18 and the common voltage applied to electrode 16. Alternatively each capillary tube 14 may be positioned between a single pair of common electrodes and subjected to the same voltage difference.

The cartridge of the present invention can be used for capillary electrophoresis or capillary IEF. The conductive substance in the capillary tubes may be a liquid solution such as a buffer or biological fluid in capillary electrophoresis, or a mixture containing sample and ampholytes in IEF. The conductive substance may also be a gel. One advantage of the present invention is that the conductive substance is confined to a short capillary tube segment which is scanned in situ by the electrophoresis instrument when separation is complete. Adequate separations have been accomplished in 30 mm long segments shortening analysis time. After scanning, the disposable cartridge containing all parts of the separation system which have come in contact with the sample may be discarded. Liquid waste generated by wash cycles is completely eliminated and the total volume of waste is drastically reduced.

Another advantage of the present invention is its ability to auto-load a quantitative sample volume when a bulk sample is applied to the cartridge. Slow competitive removal of material from the sample reservoir by a selectively absorbent material eliminates the need for a complicated auto-sampling system. This reduces the cost of the instrument as well as reducing the waste generated.

EXAMPLE 1

IEF of Cy5-HSA Utilizing Differential Sample Loading

Differential sample loading was accomplished by placing an absorbent material between the conductive film electrode and the underlying plastic support. Excess sample is removed from the conductive film after the sample has been quantitatively loaded into the capillary tube through a small hole in the conductive film. In IEF the capillary tube is filled with a mixture of sample and ampholytes by capillary action. In CE a sample plug is electrokinetically injected into a buffer filled capillary tube.

Human serum albumin (HSA), fraction V, was obtained from Sigma Chemical Company (St. Louis, Mo.). Cy5 labeled HSA was synthesized by the coupling of Cy5 fluorescent dye (Biological Detection Systems, Inc., Pittsburgh, Pa.) to HSA. Cy5-HSA was added to a 2 percent solution of ampholytes having a pH range of 3 to 10 (Biorad Inc., Hercules, Calif.) to a final Cy5-HSA concentration of 10 mg/ml. A capillary (Polymicro Technologies Inc., Phoenix, Ariz.), having an inside diameter of 100 microns and an outside diameter of 365 microns, was coated to prevent electroendosmosis (Capillary Electrophoresis, Academic Press, Inc., San Diego, Calif. (1992), pp. 191–214).

The capillary was placed in the fixture described in FIGS. 4 and 5. A double coated pressure sensitive adhesive film (RX264-S, Coating Sciences Inc., Bloomfield, Conn.) was used to bond 601-25 cellulose blotting paper (Intermountain Scientific Corporation, Bountiful, Utah) to the underlying cartridge support structure 12. The conductive plastic film with adhesive on one side (AR clad 8010, Adhesive Research Inc., Glenrock, Pa.) was bonded to the cellulose blotting paper. A hole with a diameter of 3/64 inch was punched through the conductive plastic film allowing direct access to the cellulose blotting paper beneath.

A drop (5 microliter) of the Cy5-HSA solution was placed upon the conductive film, concentric with the hole, and in contact with the end of the capillary. Within two seconds the solution filled the capillary. After thirty seconds, excess solution had completely wicked into the cellulose blotting paper. A drop (5 microliter) of 0.02 M sodium hydroxide, thickened to a viscosity of 1000 cp, was then placed upon the conductive film concentric with the hole and in direct contact with the end of the capillary. A drop of 0.02 M phosphoric acid, thickened to a viscosity of 1000 cp, was applied to the other end of the capillary in similar fashion. These drops bridged the capillary to the cathode and the anode.

Electrophoresis was performed at 1 kV constant voltage for ten minutes with a CZE 1000 R high voltage supply (Spellman Corp., Plainville, N.J.). Current was allowed to drop from 30 to 2 microamps as focusing took place. The position of the fluorescent proteins was determined at this point by scanning the capillary with a He-Ne laser optic system. A translation stage moved the cartridge relative to the optic system while the focusing field remained on. Reflected fluorescence was detected with a R928 PMT and the data was collected using data acquisition software on an IBM (trademark) personal computer.

Figure 8:
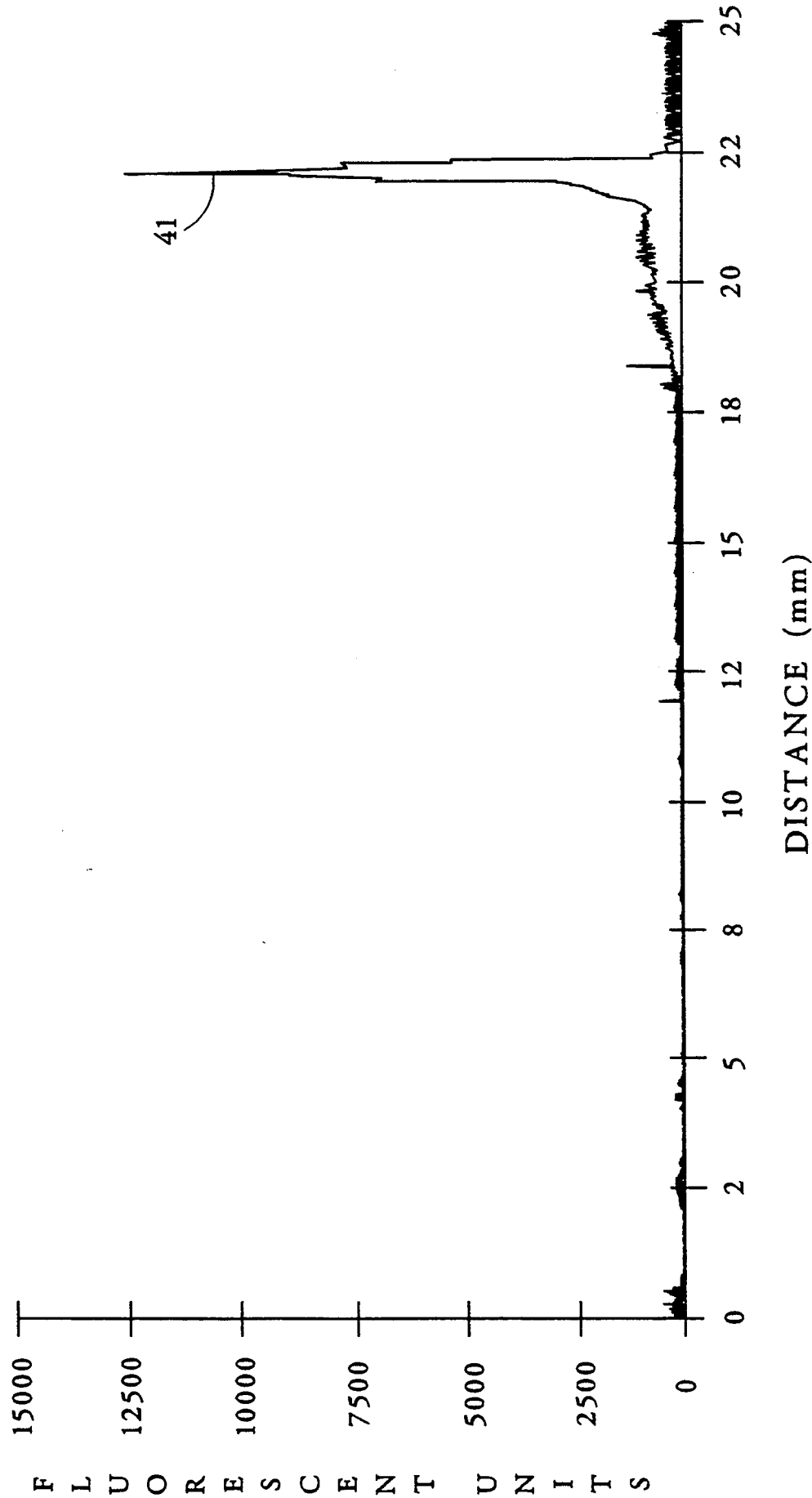
FIG. 8 shows the isoelectric focusing of Cy5 labeled HSA utilizing the auto-loading system.

Separation in this capillary system is based on the isoelectric points of the proteins. Results are shown as a plot of fluorescence versus distance on the capillary in FIG. 8. A single peak 41 corresponding to Cy5-HSA is focused. The excess solution in the cellulose blotting paper does not adversely affect the focusing of Cy5-HSA.

EXAMPLE 2

Detection of Proteins Present in Human Blood

Creatine kinase is an enzyme present in various mammalian tissue. It occurs in three different forms known as isoenzymes: CK-MM (skeletal), CK-MB (cardiac) and CK-BB (brain). After release from tissue and on circulation in blood the MM and MB forms themselves breakdown to smaller fragments known as isoforms or subforms. In the event of myocardial infarction, the MB isoenzyme, present in cardiac muscle, is released in the plasma. Hence, it serves as a specific diagnostic molecular marker for cardiac ischemia or necrosis. The early and rapid detection of this isoenzyme and its isoforms are very crucial for the diagnosis of myocardial infarction and for initiating thrombotic therapy.

Separation of Cy5 labeled CK-MB antibody from its immune complex was performed using a capillary isoelectric focusing system. CK-MB2 (human heart) and monoclonal anti CK-MB were obtained from Biospecific (Emeryville, Calif.). Fab fragments were prepared by digesting the monoclonal anti CK-MB with the enzyme papain. Cy5 labeled Fab was synthesized by the coupling of Cy5 fluorescent dye (Biological Detection Systems, Pittsburgh, Pa.) to Fab and purified by conventional gel permeation and ion exchange methods. This fluorescent substance is the labeled binding agent.

Differential separation assay (DSA) was done as follows: Cy5 labeled Fab (binding agent) was incubated with CK-MB2 (target) at a final concentration of 50 $\mu$g/ml Cy5-Fab and 1 mg/ml CK-MB2 in 1 mM phosphate 15 mM NaCl pH 7.2. A control sample consisted of Cy5-Fab alone at 50 $\mu$g/ml without added CK-MB2. Reactions were performed in 1.5 ml Eppendorf tubes in a total reaction volume of 10 $\mu$l. After incubating the samples at room temperature (20° C.) for 30 minutes, HSA was added as a carrier at a final concentration of 2 mg/ml. The reaction mixture was then diluted 30-fold with a 2% solution of ampholytes having a pH range of 3 to 10 (Biorad Inc., Hercules, Calif.) in deionized water. Capillary action was used to fill a 50×0.3×0.03 mm borosilicate glass rectangular capillary (R&S Medical, Mountain Lakes, N.J.), coated to suppress electroendosmosis (*Capillary Electrophoresis*, Academic Press, Inc., San Diego, Calif. (1992), pp. 191–214), by dipping its end in the diluted reaction mixture. The capillary was then placed horizontally on an acrylic platform and platinum electrodes were bonded to the acrylic adjacent to the ends of the capillary. A drop of 0.02 M sodium hydroxide, thickened to a viscosity of 100 cp, was applied to one end of the capillary to bridge it with the cathodic electrode and a drop of 0.02 M phosphoric acid was applied to the other end of the capillary to bridge it with the anode. Electrophoresis was performed at 2 kV constant voltage for 10 minutes with a CZE 1000R high voltage supply (Spellman, Plainville, N.J.). The current was allowed to drop from 30 to 2 $\mu$amps as the focusing took place.

The positions of the fluorescent proteins were determined at this point by scanning the capillary with a He-Ne laser optic system. A translation stage moved the capillary while the focusing field remained on. The reflected fluorescence was detected with a R928 PMT and the data was collected using data acquisition software on an IBM (trademark) personal computer.

Figure 9:
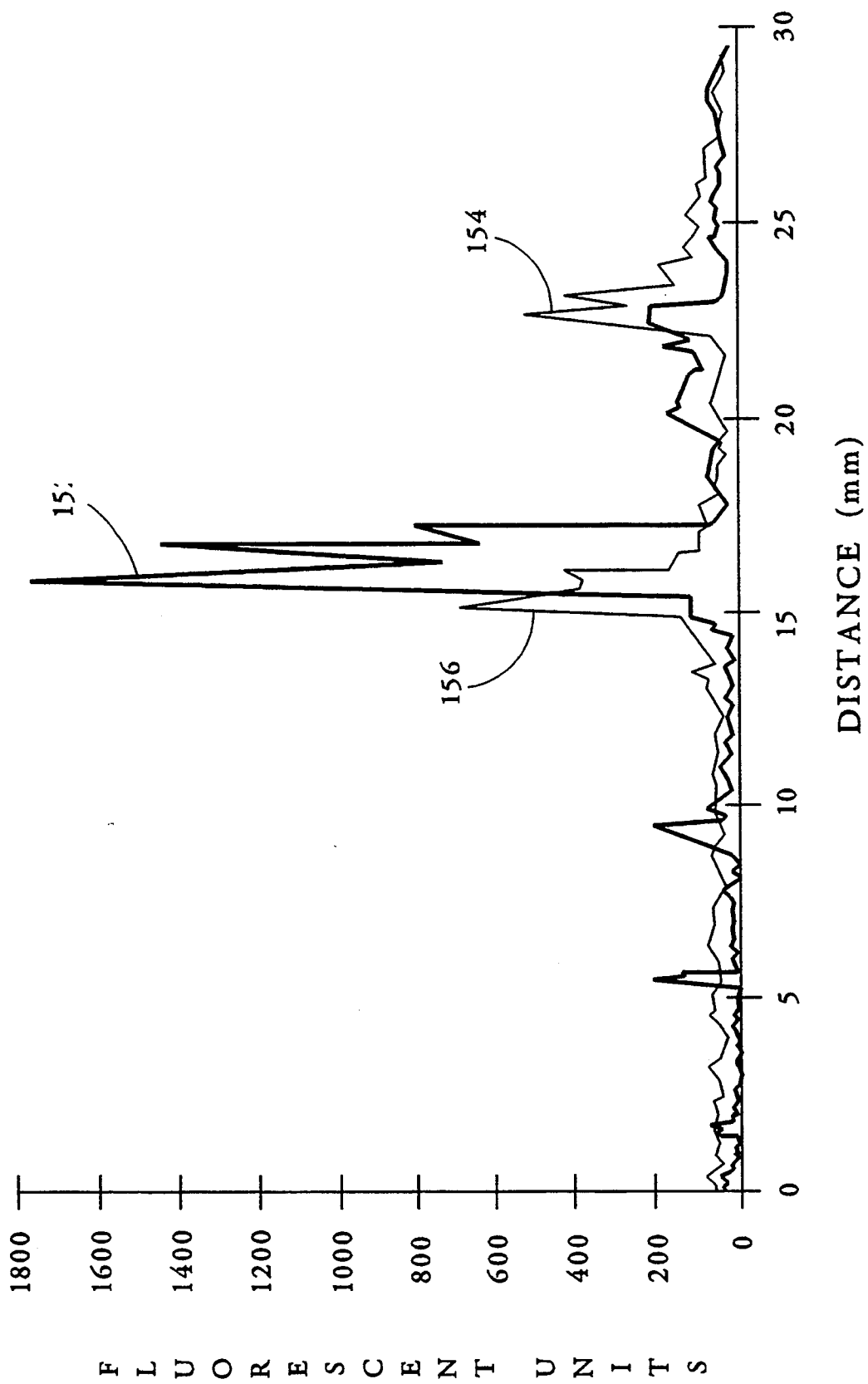
FIG. 9 shows the isoelectric focusing of Cy5 labeled Fab and Cy5 labeled Fab complexed with CKMB2 in a capillary segment.

Separation in this capillary system is based on the isoelectric points of the proteins. The results are shown as a plot of fluorescence versus distance on the capillary in FIG. 9. When Cy5-Fab alone is run a Cy5-Fab control peak 152 is focused at 18 mm. When CK-MB2 is present a second peak 154 corresponding to the immune complex consisting of Cy5-Fab/CK-MB2 is focused at 23 mm while a peak 156 corresponding to the residual uncomplexed labeled Cy5-Fab is focused at 15 mm.

We claim:

1. A single use cartridge for an electrophoresis instrument comprising:
   a support structure;
   at least one capillary tube horizontally disposed by said support structure, said capillary tube having longitudinally opposed ends; and
   electrodes formed on said structure adjacent to said capillary ends, said electrodes being planar electrically conductive films disposed beneath said capillary tube ends adapted for electrical contact with said capillary ends when said capillary tube is filled with a conductive liquid solution, said conductive liquid solution being statically confined in said capillary tube, said film being a homogenously conductive plastic,
   whereby an electromotive force is produced along said capillary tube by connecting the pair of electrodes located at opposite ends of said capillary tube to an external voltage supply when said capillary tube is filled with said conductive substance.

2. The cartridge of claim 1 wherein said capillary tube is disposed in a V-shaped groove in said support structure.

3. A single use cartridge for an electrophoresis instrument comprising:
   a support structure;
   at least one capillary tube horizontally disposed by said support structure, said capillary tube having longitudinally opposed ends; and
   electrodes formed on said structure adjacent to said capillary ends, said electrodes being planar electrically conductive films disposed beneath said capillary tube ends adapted for electrical contact with said capillary ends when said capillary tube is filled with a conductive liquid solution and a drop of an electrically conductive substance is disposed at said capillary tube end on said electrode, said conductive substance having a viscosity sufficient to reduce hydrodynamic flow within said conductive liquid solution statically confined in said capillary tube,
   whereby an electromotive force is produced along said capillary tube by connecting the pair of electrodes located at opposite ends of said capillary tube to an external voltage supply when said capillary tube is filled with said conductive liquid solution.

4. A single use cartridge for an electrophoresis instrument comprising:
   a support structure;
   at least one capillary tube horizontally disposed by said support structure, said capillary tube having longitudinally opposed ends; and
   electrodes formed on said structure adjacent to said capillary ends, said electrodes being planar electrically conductive films disposed beneath said capillary tube ends adapted for electrical contact with said capillary ends when said capillary tube is filled with a conductive liquid solution, said capillary tube being filled by capillary action when said conductive liquid solution is placed on said electrode at said tube end, said conductive liquid solution being statically confined in said capillary tube,
   whereby an electromotive force is produced along said capillary tube by connecting the pair of electrodes located at opposite ends of said capillary tube to an external voltage supply when said capillary tube is filled with said conductive liquid solution.

5. A single use cartridge for an electrophoresis instrument comprising:
   a support structure;
   at least on capillary tube supported by said structure, said capillary tube being formed by ultrasonically welding two injection molded plastic parts together, said capillary tube further having longitudinally opposed ends; and
   electrodes formed on said structure adjacent to said capillary ends, said electrodes being adapted for electrical contact with said capillary ends when said capillary tube is filled with a conductive substance, said conductive substance being statically confined in said capillary tube,
   whereby an electromotive force is produced along said capillary tube by connecting the pair of electrodes located at opposite ends of said capillary tube to an external voltage supply when said capillary tube is filled with said conductive substance.

6. A single use cartridge for an electrophoresis instrument comprising:
   a support structure;
   at least on capillary tube supported by said structure, said capillary tube having longitudinally opposed ends and a length less than six centimeters; and
   electrodes formed on said structure adjacent to said capillary ends, said electrodes being adapted for electrical contact with said capillary ends when said capillary tube is filled with a conductive substance, said conductive substance being statically confined in said capillary tube,
   whereby an electromotive force is produced along said capillary tube by connecting the pair of electrodes located at opposite ends of said capillary tube to an external voltage supply when said capillary tube is filled with said conductive substance.

7. A single use cartridge for an electrophoresis instrument comprising:
   a support structure;
   a plurality of capillary tubes supported by said structure, each of said capillary tubes having longitudinally opposed ends; and
   electrodes formed on said structure adjacent to said capillary ends, each of said capillary tube ends being adjacent to one of said electrodes, said electrodes being adapted for electrical contact with said capillary tube ends when said capillary tube is filled with a conductive substance, said conductive substance being statically confined in said capillary tube,
   whereby an electromotive force is produced along said capillary tube by connecting the pair of electrodes located at opposite ends of said capillary tube to an external voltage supply when said capillary tube is filled with said conductive substance.

8. The cartridge of claim 9 including a plurality of said electrodes.

9. The cartridge of claim 8 wherein one end of each of said capillary tubes is adjacent to a first common electrode.

10. The cartridge of claim 9 wherein each of said capillary tubes has the other end adjacent to a second common electrode.

11. The cartridge of claim 7 wherein said capillary tubes are disposed in a coplanar array.

12. The cartridge of claim 7 wherein said capillary tubes are of equal length and equal cross-sectional dimension.

13. A single use cartridge for an electrophoresis instrument comprising:
   a support structure;
   at least one capillary tube supported by said structure, said capillary tube being permanently attached to said support structure and having longitudinally opposed ends; and
   electrodes formed on said structure adjacent to said capillary ends, said electrodes being adapted for electrical contact with said capillary ends when said capillary tube is filled with a conductive substance, said conductive substance being statically confined in said capillary tube,
   whereby an electromotive force is produced along said capillary tube by connecting the pair of electrodes located at opposite ends of said capillary tube to an external voltage supply when said capillary tube is filled with said conductive substance.

14. A single use cartridge for an electrophoresis instrument comprising:
   a support structure;
   at least one capillary tube supported by said structure, said capillary tube having longitudinally opposed ends and a high surface area to volume ratio; and
   electrodes formed on said structure adjacent to said capillary ends, said electrodes being adapted for electrical contact with said capillary ends when said capillary tube is filled with a conductive substance, said conductive substance being statically confined in said capillary tube,
   whereby an electromotive force is produced along said capillary tube by connecting the pair of electrodes located at opposite ends of said capillary tube to an external voltage supply when said capillary tube is filled with said conductive substance.

15. A single use cartridge for an electrophoresis instrument comprising:
   a support structure;
   at least one optically transparent capillary tube supported by said structure, said capillary tube having longitudinally opposed ends; and
   electrodes formed on said structure adjacent to said capillary ends, said electrodes being adapted for electrical contact with said capillary ends when said capillary tube is filled with a conductive substance, said conductive substance being statically confined in said capillary tube, whereby an electromotive force is produced along said capillary tube by connecting the pair of electrodes located at opposite ends of said capillary tube to an external voltage supply when said capillary tube is filled with said conductive substance.

16. A single use cartridge for an electrophoresis instrument comprising:

a support structure;

at least one capillary tube supported by said structure, said capillary tube being rectangular in cross-section with a large aspect ratio, said capillary tube having longitudinally opposed ends; and electrodes formed on said structure adjacent to said capillary ends, said electrodes being adapted for electrical contact with said capillary ends when said capillary tube is filled with a conductive substance, said conductive substance being statically confined in said capillary tube, whereby an electromotive force is produced along said capillary tube by connecting the pair of electrodes located at opposite ends of said capillary tube to an external voltage supply when said capillary tube is filled with said conductive substance.

17. A single use cartridge for an electrophoresis instrument comprising:

a support structure;

at least one capillary tube supported by said structure, said capillary tube being formed by joining separate plastic parts together, said capillary tube further having longitudinally opposed ends; and electrodes formed on said structure adjacent to said capillary ends, said electrodes being adapted for electrical contact with said capillary ends when said capillary tube is filled with a conductive substance, said conductive substance being statically confined in said capillary tube, whereby an electromotive force is produced along said capillary tube by connecting the pair of electrodes located at opposite ends of said capillary tube to an external voltage supply when said capillary tube is filled with said conductive substance.

18. The cartridge of claim 17 wherein one of said plastic parts is a thin film.

19. A single use cartridge for an electrophoresis instrument comprising:

a support structure;

at least one capillary tube supported by said structure, said capillary tube having longitudinally opposed ends; and electrodes formed on said structure adjacent to said capillary ends, said electrodes being adapted for electrical contact with said capillary ends when said capillary tube is filled with a conductive substance, said conductive substance containing a surfactant and being statically confined in said capillary tube, whereby an electromotive force is produced along said capillary tube by connecting the pair of electrodes located at opposite ends of said capillary tube to an external voltage supply when said capillary tube is filled with said conductive substance.

20. A disposable cartridge for an electrophoresis instrument comprising:

a support structure;

at least one electrophoretic pathway supported by said structure;

a first reservoir adapted for application of a bulk sample, said first reservoir being in material communication with said pathway;

auto-loading means for quantitatively drawing a selected sample volume into said pathway from said first reservoir at a first rate;

a second reservoir in material communication with said first reservoir; and means for moving material from said first reservoir to said second reservoir at a second rate, said first rate being much faster than said second rate, whereby all remaining material in said first reservoir is moved into said second reservoir after said selected sample volume has been quantitatively loaded into said pathway.

21. The cartridge of claim 20 wherein said pathway has longitudinally opposed ends and said first reservoir is located at one of said ends.

22. The cartridge of claim 20 wherein said auto-loading means comprises the filling of a capillary segment by capillary action.

23. The cartridge of claim 20 wherein said second reservoir comprises an absorbent material in fluid communication with said first reservoir.

24. The cartridge of claim 23 wherein said absorbent material is selectively absorbent.

25. The cartridge of claim 21 further comprising electrodes formed on said structure adjacent said pathway ends.

26. The cartridge of claim 25 wherein said first reservoir is located between said pathway end and said adjacent electrode.

27. The cartridge of claim 26 wherein said adjacent electrode is spaced apart from said pathway end and said first reservoir comprises an open-sided gap between said pathway end and said adjacent electrode.

28. The cartridge of claim 27 wherein said electrodes comprise planar conductive films.

29. The cartridge of claim 28 wherein said film is metalized plastic.

30. The cartridge of claim 28 wherein said electrically conductive film is a homogenously conductive plastic.

31. The cartridge of claim 28 wherein said pathway is a horizontally disposed capillary tube, said capillary ends being disposed above said electrodes.

32. The cartridge of claim 31 wherein said capillary tube is made of plastic, glass or silica.

33. The cartridge of claim 31 wherein said capillary is round, rectangular or square in cross-section.

34. The cartridge of claim 31 wherein said capillary is optically transparent.

35. The cartridge of claim 34 wherein said capillary tube is rectangular with a large aspect ratio.

36. The cartridge of claim 20 wherein said pathway has longitudinally opposed ends further comprising electrodes formed on said structure, said electrodes being disposed adjacent to said ends and said first reservoir, and wherein said auto-loading means comprises electrokinetic injection.

37. The cartridge of claim 20 comprising a plurality of pathways, each pathway in material communication with one of a plurality of first reservoirs wherein a sample is simultaneously loaded into each of said pathways by one of a plurality of auto-loading means.

38. A disposable cartridge for use in an electrophoresis instrument comprising:

a support structure;

a plurality of horizontally disposed capillary-sized electrophoretic pathways having longitudinally opposed ends supported by said structure;

a plurality of thin-film planar electrodes supported by said structure such that each end of each of said pathways is located adjacent to one of said electrodes, said adjacent electrode being disposed beneath said pathway end, each of said electrodes having an exposed surface remote from said pathway end adapted for connection to an external voltage supply; and each of said pathway ends being closely spaced apart from said adjacent electrode forming a gap therebetween, said gap being adapted for application of material such that application of an electrically conductive substance to said gap electrically bridges said pathway end to said adjacent electrode, whereby an electromotive force is produced along one of said pathways by connecting the pair of electrodes located at opposite ends of said pathway to an external voltage supply after said gap has been bridged by an electrically conductive substance.

39. The cartridge of claim 38 further comprising autoloading means for quantitatively loading a selected amount of material from said gap into said pathway when a larger amount of material is applied to said gap.

40. The cartridge of claim 39 wherein said auto-loading means comprises filling of a capillary segment by capillary action.

41. The cartridge of claim 39 wherein said auto-loading means comprises electrokinetic injection.

42. The cartridge of claim 39 further comprising absorbent means supported by said structure in material communication with said gap for selectively removing material from said gap at a controlled rate such that excess material is removed from said gap after a selected amount of material has been quantitatively loaded from said gap into said pathway.

43. A disposable cartridge for an electrophoresis instrument comprising:

a support structure;

at least one electrophoretic pathway supported by said structure, said pathway having longitudinally opposed ends;

electrodes formed on said structure adjacent to said pathway ends, said electrodes being adapted for electrical contact with said pathway ends, at least one of said pathway ends being spaced apart from said adjacent electrode forming a gap therebetween, said gap being adapted for the introduction of material between said electrode and said adjacent pathway end;

means for quantitatively applying a selected volume of material from said gap into said pathway; and absorbent means formed on said structure in material communication with said gap for selectively removing material from said gap at a controlled rate, whereby excess material is removed from said gap after quantitative application of a selected volume of material from said gap into said pathway.

* * * * *

UNITED STATES PATENT AND TRADEMARK OFFICE
CERTIFICATE OF CORRECTION

PATENT NO. : 5,338,427
DATED : August 16, 1994
INVENTOR(S) : Robert J. Shartle and Robert S. Dubrow It is certified that error appears in the above-indentified patent and that said Letters Patent is hereby corrected as shown below:

Column 11, line 26, delete "on" and insert therefor --one--.

Column 11, line 45, delete "on" and insert therefor --one--.

Column 12, line 10, delete "9" and insert therefor --7--.

Signed and Sealed this

Seventh Day of May, 1996

Attest:

BRUCE LEHMAN

Attesting Officer

Commissioner of Patents and Trademarks